(12) United States Patent
Lin (10) Patent No.: US 12,171,521 B2
(45) Date of Patent: Dec. 24, 2024

(54) AMBULATORY AND CENTRALIZED PROCESSING OF A PHYSIOLOGICAL SIGNAL

(71) Applicant: Braemar Manufacturing, LLC, Eagan, MN (US)

(72) Inventor: Dongping Lin, Irvine, CA (US)

(73) Assignee: BRAEMAR MANUFACTURING, LLC, Eagan, MN (US)

( * ) Notice: Subject to any disclaimer, the term of this patent is extended or adjusted under 35 U.S.C. 154(b) by 556 days.

(21) Appl. No.: 16/823,982

(22) Filed: Mar. 19, 2020

(65) Prior Publication Data

US 2020/0214563 A1 Jul. 9, 2020

Related U.S. Application Data

(63) Continuation of application No. 12/413,290, filed on Mar. 27, 2009, now Pat. No. 9,655,518, and a continuation of application No. 15/598,021, filed on May 17, 2017, now Pat. No. 10,660,520, which is a continuation of application No. 12/413,290, filed on Mar. 27, 2009, now Pat. No. 9,655,518.

(51) Int. Cl.
*A61B 5/00* (2006.01)

(52) U.S. Cl.
CPC ................. *A61B 5/0002* (2013.01)

(58) Field of Classification Search
CPC ..... A61B 5/0006; A61B 5/002; A61B 5/0022; A61B 5/0402; A61B 5/1112; A61B 5/7264; A61B 5/565; G06F 19/3418; G06F 19/345; G08B 21/02
See application file for complete search history.

(56) References Cited

U.S. PATENT DOCUMENTS

| | | | |
|---|---|---|---|
| 6,416,471 B1* | 7/2002 | Kumar | A61B 5/0022 128/903 |
| 2006/0064030 A1* | 3/2006 | Cosentino | A61B 5/0022 128/920 |
| 2008/0001735 A1* | 1/2008 | Tran | A61B 5/6803 340/539.22 |

* cited by examiner

*Primary Examiner* — Deborah L Malamud (57) ABSTRACT

A machine-implemented method including obtaining physiological signal data for a living being and performing a first analysis of the physiological signal data at a processing device local to the living being and remote from a central processing device. The method further includes transmitting from the processing device data associated with the analysis to the central processing device and performing at the central processing device a second analysis of the data associated with the first analysis. The method further includes displaying the data associated with the second analysis. The method can also include interaction between the processing device local to the living being and the central processing device. The method can also include distributing monitoring and analysis between an ambulatory and a centralized subsystem.

18 Claims, 4 Drawing Sheets

AMBULATORY AND CENTRALIZED PROCESSING OF A PHYSIOLOGICAL SIGNAL

CROSS-REFERENCE TO RELATED APPLICATION

This application is a continuation of U.S. patent application Ser. No. 15/598,021, filed May 17, 2017 (now U.S. Pat. No. 10,660,520) which is a continuation of U.S. patent application Ser. No. 12/413,290 filed Mar. 27, 2009 (now U.S. Pat. No. 9,655,518) which are herein incorporated by reference in their entirety.

BACKGROUND

Physiological activity of various organs, such as the heart or brain, can be monitored, and this physiological activity can be analyzed to look for patterns that may assist in diagnosing various conditions. For example, the electrical activity of the heart can be monitored to track various aspects of the functioning of the heart. Cardiac monitoring devices sense the cardiac electrical activity of a living being. Cardiac electrical activity can be indicative of disease states or other physiological conditions ranging from benign to fatal.

SUMMARY

In a first aspect, a machine-implemented method includes obtaining first physiological signal data for a living being, performing a first analysis of the first physiological signal data at a first processing device local to the living being and remote from a central processing device. The method further includes transmitting from the first processing device data associated with the first analysis to the central processing device. The method further includes performing at the central processing device a second analysis of the data associated with the first analysis. The method further includes displaying the data associated with the second analysis.

Implementations can include any, all, or none of the following features. The first physiological signal data can include cardiac signal data; performing a first analysis of the physiological signal data can include determining arrhythmia events in the cardiac signal data; and the data associated with the first analysis can include the physiological signal data associated with arrhythmia events. The machine-implemented method can include receiving feedback data at the central processing device from a health care professional regarding the data associated with the first or second analysis; and automatically adjusting configuration settings at either the central processing device or at the first processing device based on the health care professional's feedback. The machine-implemented method can include transmitting configuration settings from the central processing device to the first processing device based on the second analysis; and adjusting the first processing device based on the configuration settings. Transmitting configuration settings from the central processing device can include transmitting configuration settings to redistribute at least a portion of an analysis performed at the first processing device to the central processing device. Transmitting configuration settings from the central processing can include transmitting configuration settings to adjust a type of analysis performed at the first processing device. The machine-implemented method can include transmitting data requests to the first processing device; transmitting requested data from the first processing device to the remote central processing device based on the data request; and analyzing the requested data at the remote central processing device. The machine-implemented method can include transmitting a request to the first processing device for additional analysis to be performed by the first processing device; performing the additional analysis at the first processing device; and transmitting data associated with the additional analysis to the central processing device.

The machine-implemented method can also include where obtaining first physiological signal data can include obtaining electrocardiogram (ECG) data; wherein performing a first analysis of the first physiological signal data can include determining QRS data for multiple QRS complexes in the ECG data; where transmitting data associated with the first analysis can include transmitting the QRS data; and where performing a second analysis can include performing an analysis to determine heart rate variability. The machine-implemented method can include obtaining second physiological signal data for a second living being; performing a first analysis of the second physiological signal data at a second processing device local to the second living being and remote from the central processing device; transmitting from the second processing device data associated with the first analysis of the second physiological signal data to the central processing device; performing at the central processing device a second analysis of the data transmitted from the second processing device; and displaying the data associated with the second analysis.

The machine-implemented method can also include obtaining second physiological signal data for a second living being; performing a first analysis of the second physiological signal data at a second processing device local to the second living being and remote from the central processing device; transmitting from the second processing device data associated with the first analysis of the second physiological signal data to the central processing device; performing at the remote central processing device a second analysis of the data transmitted from the second processing device; comparatively analyzing the data associated with the second analysis of the data transmitted from the second processing device and the data associated with the second analysis of the data transmitted from the first processing device; and transmitting configuration settings to the first or the second processing device based on the comparative analysis. The machine-implemented method can include comparatively analyzing data associated with the second analysis with data associated with an analysis of a physiological signal for the living being from a different time period.

The machine-implemented method can also include obtaining second physiological signal data for a second living being; transmitting the second physiological signal data from a second processing device local to the second living being and remote from the central processing device to the central processing device as the second physiological data is obtained; and performing at the central processing device an analysis of the data transmitted from the second processing device as the data is received at the central processing device.

In a second aspect, a system includes a monitoring apparatus local to a living being and remote from a central processing device, the monitoring apparatus configured to perform operations including obtaining physiological signal data for the living being, performing a first analysis of the physiological signal data, and transmitting data associated with the first analysis. The system further includes the central processing device configured to receive the transmitted data associated with the first analysis and to perform a second analysis of the data associated with the first analysis. The system further includes a display for displaying data associated with the second analysis.

Implementations can include any, all, or none of the following features. The physiological signal data can include cardiac signal data; wherein performing a first analysis of the physiological signal data can include determining atrial fibrillation events in the cardiac signal data; and wherein the data associated with the first analysis can include the physiological signal data associated with atrial fibrillation events. The central processing device can be further configured to transmit configuration settings to the monitoring apparatus; and where the monitoring apparatus makes adjustments based on configuration settings. The adjustments can include adjustments to the amount or type of analysis performed at the first processing device. The central processing device can be further configured to receive feedback from a health care professional regarding the data associated with the second analysis and to automatically determine the configuration settings based on the health care professional's feedback. The monitoring apparatus can be further configured to transmit a request to the monitoring apparatus for additional analysis to be performed by monitoring apparatus. The central processing device can be further configured to transmit data requests to the monitoring apparatus; and where the monitoring apparatus can be further configured to perform the step of transmitting data based on the data request to the central processing device. The data associated with the first analysis can include analysis results.

The physiological signal can include ECG data; wherein the first analysis can include determining multiple QRS complexes in the ECG data; wherein the data associated with the first analysis can include fiducial points for the multiple QRS complexes; and wherein the second analysis can include determining heart rate variability. The system can include a second monitoring apparatus local to a second living and remote from the central processing device being configured to perform the steps including obtaining second physiological signal data for the second living being, performing a first analysis of the second physiological signal data, and transmitting data associated with the first analysis of the second physiological signal data to the central processing device; and wherein the central processing device can be configured to receive the transmitted data associated with the first analysis of the second physiological signal data via a communications channel and to perform a second analysis of the data associated with the first analysis of the second physiological signal data. The system can include a second monitoring apparatus local to a second living being and remote from the central processing device configured to perform the steps including obtaining second physiological signal data for the second living being, transmitting the second physiological signal data to the central processing device as the second physiological data can be obtained; and wherein the central processing device can be configured to analyze the second physiological signal data as the second physiological signal data can be received by the central processing device.

In a third aspect, a system includes multiple processing apparatuses. The system further includes each of the multiple processing apparatuses having a computer-readable storage device having a computer program product encoded therein, the computer program product operable to cause each of the respective multiple processing apparatuses to perform operations including obtaining a physiological signal data for a living being local to each of the respective processing apparatuses, performing a first analysis of the physiological signal data, and transmitting data associated with the first analysis to a computer remote from the multiple patients. The system further includes a remote computer-readable storage device remote from the multiple patients having a computer program product encoded therein, the computer program product operable to cause the remote computer to perform operations including performing at the remote central processing system a second analysis of the data associated with each of the first analyses, and displaying the data associated with the each of the second analyses on one or more monitoring stations.

Implementations can include any, all, or none of the following features. The physiological signal data can include cardiac signal data; wherein performing a first analysis of the physiological signal data can include determining arrhythmia events in the cardiac signal data; and wherein the data associated with the first analysis can include the physiological signal data associated with arrhythmia events. The computer program product of the remote computer-readable storage device can be further operable to cause the remote computer to perform operations including transmitting configuration settings to each of the multiple processing apparatuses based on each of the respective second analyses of the data associated with each of the first analyses; and wherein the computer program product of each of the multiple processing apparatuses can be further operable to cause each of the respective processing apparatuses to perform the operations including adjusting each processing apparatus based on the configuration settings. The remote computer-readable storage device can be further operable to cause the remote computer to perform operations can include automatically determining configuration settings based on feedback received from one or more health care professionals. The remote computer-readable storage device can be further operable to cause the remote computer to perform operations including comparatively analyzing the data associated with the each of the second analyses; determining configuration settings for one or more of the multiple processing apparatuses based on the comparative analysis; and transmitting the configuration settings to the one or more of the multiple processing apparatuses.

The details of one or more implementations are set forth in the accompanying drawings and the description below. Other features, aspects, and advantages will be apparent from the description and drawings, and from the claims.

DESCRIPTION OF DRAWINGS

Like reference symbols in the various drawings indicate like elements.

DETAILED DESCRIPTION

Figure 1:
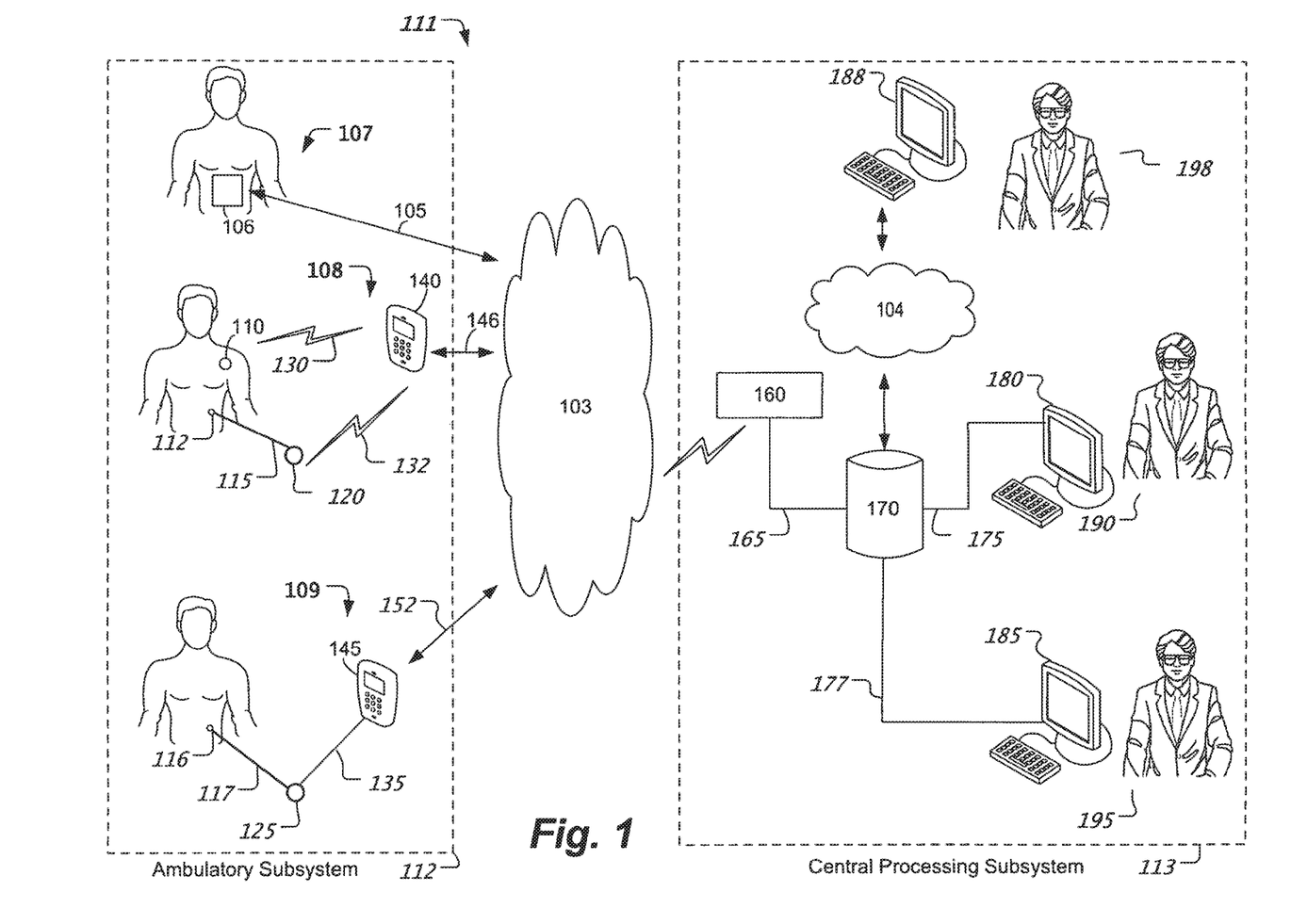
FIG. 1 shows an example system for monitoring one or more patients with interactive ambulatory and central processing capabilities.

FIG. 1 shows an example system 111 for monitoring one or more patients with interactive ambulatory and central processing capabilities. The system 111 can monitor data related to various physiological signals such as cardiac signals. The system 111 can monitor, for example, a cardiac signal for occurrence of events such as arrhythmia events including atrial fibrillation (AF) events. The system 111 includes an ambulatory subsystem 112 and a central processing subsystem 113 that can communicate with each other via a network 103.

The ambulatory subsystem 112 can include one or more monitoring apparatuses that are remote from the central processing subsystem 113 for monitoring physiological data from one or more patients. Example monitoring apparatuses are shown at 107, 108, and 109, each including a processing device or processing apparatus that can analyze a physiological signal. A monitoring apparatus can include, for example, an implantable medical device (IMD), (e.g. an implantable cardiac defibrillator and an associated transceiver or a pacemaker and an associated transceiver), or a monitoring device that a patient wears.

An example monitoring apparatus 107 includes both a processing device and a sensor or sensors integrated into a single device 106 that a patient wears. The monitoring apparatus 107 analyzes data from the sensor or sensors. Sensor data can include raw physiological signal data, such as Electrocardiogram (ECG) data or heart beat data. The monitoring apparatus 107 can also transmit data to the central processing subsystem over network 103 using a communications link 105 which can be a wired or wireless communications link.

Another example monitoring apparatus 108 includes a processing device 140 and a sensor 110 attached to a patient. The sensor 110 obtains physiological signal data from the patient and transmits that data over a wireless communications link 130 to the processing device 140. Monitoring apparatus 108 can also include a sensor 120 that obtains data related to a physiological signal from the patient across a lead 115 and transmits that data to the processing device 140 over a wireless communications link 132. The lead 115 connects to a physiological data sensing device 112, such as an electrode, attached to the patient's body. The handheld device 140 analyzes the data received from the sensor or sensors 110 and 120. The processing device 140 can transmit data using the communications link 146 over the network 103 to the central processing subsystem. The communications link 146 can be a wired or wireless communications link. In some examples, the data analysis capability can be performed by sensors 110 and 120, or by the hand-held device, or by a combination of the sensors 110, 120 and the hand-held device 140.

Another example monitoring apparatus 109 includes a processing device 145, a sensor 125 and a lead wire 117. The lead 117 connects to physiological data sensing device 116, such as an electrode, attached to the patient's body. The sensor 125 can have analysis process capability. The sensor 125 obtains data associated with a physiological signal across the lead wire 117 and transmits that data via a wired link 135 to the handheld device 145. The handheld device 145 can analyze the data received from the sensor 125 and can transmit data to the central processing subsystem 113 over network 103 using communications link 152, which can be wired or wireless.

Monitoring apparatus, such as those shown at 107, 108, and 109, can analyze the data associated with a physiological signal, such as ECG signal, pulse oximetry Spo2 signal, respiratory signal, etc. The analysis can be performed real-time as the data is received. The monitoring apparatus can transmit data associated with the analysis, such as the results of the analysis and/or the sensor data associated with the analysis through a communication network 103 to the central processing subsystem 113. The communications network 103 can be a local area network (LAN), a landline telephone network, a wireless network, wide-area network, a cellular network, a satellite communication network, other suitable networks to facilitate two-way communication with the central processing subsystem, or any combination of such. Examples of such networks are internet, WIFI, cellular phone, WiMAX, or a direct wire connection such as cable or a dial up modem connecting to a network through a regular phone line. Monitoring apparatuses 107, 108 and 109 can also communicate with the central processing subsystem using separate communications networks.

Real-time analysis performed in the ambulatory subsystem 112 can include, for example, identification of various physiological events such as arrhythmia events for reporting to the central processing subsystem. The real-time analysis can also include identification of various parts of a physiological signal (such as onsets, offsets, intervals, variations in intervals, normal morphology, abnormal morphology, etc), which may be needed for determining and analyzing physiological events. A monitoring apparatus, e.g. 107, 108, and/or 109, can send analysis results to the central processing subsystem 113. The monitoring apparatus can send all of the received sensor data via network 103 to the central processing subsystem 113. In some examples, sending all of the sensor data via network 103 may not be the most efficient use of data bandwidth, processing power, and battery resources. The monitoring apparatus can send selections of the sensor data. In some examples, the monitoring apparatus can send selected sensor data based on the analysis performed by the monitoring apparatus, such as sensor data corresponding to reported physiological events, such as atrial fibrillation or other cardiac events.

The central processing subsystem 113 includes one or more communications devices, such as a communications device 160, for receiving data from the ambulatory subsystem 112 via network 103 and for transmitting data from the central processing subsystem 113 to the ambulatory subsystem 112. The central processing subsystem 113 includes a central processing device 170 and one or more monitoring (or display) stations, such as monitoring stations 180 and 185. The communications device 160 transmits data received from the ambulatory subsystem 112 to the central processing device 170. The central processing device 170 can include one or more computers and/or processing devices for processing and analyzing data received from the ambulatory subsystem. The central processing device 170 can also include one or more storage devices, such as a mass storage device or a non-volatile memory device for storing data received from the ambulatory subsystem 112. The central processing device 170 can also analyze data received from the ambulatory subsystem automatically or upon request and can display the results of the analysis on one or more monitoring stations, e.g. 180 and 185 via communication links 175 and 177, which can be wired or wireless. A monitoring apparatus from the ambulatory subsystem can send raw physiological signal data across network 103 to the central processing subsystem 113 where the raw physiological signal data is analyzed real-time by the central processing system 113. In other examples, a monitoring apparatus in the ambulatory subsystem can analyze raw physiological data and send data associated with the analysis results to the central processing subsystem 113 where additional analysis is performed on the data associated with the analysis results.

One or more health care professionals, e.g. at 190 or 195, such as a cardiovascular technician (CVT), can use a monitoring station, e.g. 180 or 185, to evaluate the analysis results received from the ambulatory and/or data associated with an analysis provided by the central processing device 170. For example, the health care professional 190 can use monitoring station 180 to review analysis results generated by the central processing device 170 of data associated with a physiological signal in a patient in the ambulatory subsystem 112. At the same time, the health care professional 195 can use monitoring station 185 to review analysis results generated by the central processing device 170 of data associated with a physiological signal in another patient in the ambulatory subsystem. In some examples, the health care professional 190 and/or 195 can have the central processing device 170 perform additional analyses on the data received from the ambulatory subsystem. The health care professional 190 and/or 195 can also request additional information, such as sensor data from the central processing device 170. If the central processing device 170 does not have the requested data, it can request the data from the monitoring apparatus in the ambulatory subsystem that provided the data. In some implementations, the health care professional can provide feedback to the central processing device 170, such as accept, reject, and/or modify previously identified physiological events such as arrhythmia events. The health care professional can also identify and report additional physiological events.

The central processing device 170 also can provide analysis results to a health care professional 198, such as a doctor, via network 104 or other such network. Network 104 can be wired or wireless. The health care professional 110 can obtain the report using a computer 188 connected to a network 104. In some implementations, the network 103 and the network 104 can be the same network. They can also be different networks. The central processing subsystem 113, can include, for example, any processing device that can access the network 103 such as the internet, a cell phone network, or the like. In other examples, the health care professional 110 can receive the report using a facsimile. Based on the doctor's review, the doctor can request additional analysis and/or data from the central processing device 170 via network 104. The health care professional 198 can also provide feedback to the central processing device 170.

In some implementations, the central processing subsystem 113 can provide configuration settings to the various monitoring apparatuses in the ambulatory subsystem. For example, configuration settings can be transmitted to the various monitoring apparatuses based on a health care professional's feedback. Accordingly, the configuration settings can be tailored to the specific needs and/or prescription of the patient being monitored. For example, a health care professional such as a doctor and/or a clinician can provide changes to the configuration settings for a monitoring apparatus for a particular patient based on the analysis results provided by the central processing device 170. The analysis results can be the results from the ambulatory subsystem or the results from the analysis performed by the central processing device 170. The health care professional can provide the changes to the central processing device 170, and the communications device 160 transmits those configuration settings to the particular patient's monitoring apparatus via network 103. Changes to the configuration settings can include, for example, monitoring settings, analysis settings, the data that the monitoring apparatus transmits to the central processing subsystem, alarm settings (e.g. when to transmit an alarm), threshold settings (e.g. thresholds for determining arrhythmias), results grouping (e.g. how various arrhythmias are grouped), etc.

The central processing device 170 can also analyze the data received from the ambulatory subsystem for clinically significant events. For example, if the central processing device 170 receives raw sensor data from a monitoring device in the ambulatory subsystem, the central processing device 170 can analyze for physiological events such as arrhythmia events. In some examples, the central processing device 170 can receive sensor data associated with physiological events identified by the ambulatory subsystem. The central processing device 170 can have verification or validation capability to ensure the results generated by the ambulatory subsystem and by the central processing device 170 itself are correct. The central processing device 170 can perform cross checking between results provided by the ambulatory subsystem 112 and the central processing subsystem 113. In some examples, the central processing subsystem 113 may have more up-to-date analysis algorithms or more processing power to provide more monitoring and diagnostic capabilities which can provide more accurate results.

Having analysis capabilities in the central processing subsystem 113 can provide a health care professional (e.g. 190, 195, and 198) various advantages. For example, more monitoring and diagnostic capabilities can relatively easily be added to the central processing device 170, such as when new monitoring and diagnostic procedures are introduced. The central processing device 170 can provide health care professionals with various algorithms to choose from for analyzing the data received from the ambulatory subsystem. For example, if a health care professional determines that particular data needs to be reanalyzed, the health care professional can select an appropriate algorithm and have the server reanalyze the data. For example, reanalyzing may be needed if a health care professional does not agree with the analysis results generated by an ambulatory subsystem or a health care professional wants to perform additional diagnoses.

The central processing device 170 can learn from the decisions made by a health care professional and adjust the analysis performed by the ambulatory subsystem, the real-time analysis subsystem, or both in order help the health care professional review the monitoring and diagnostic information. When a health care professional confirms, accepts, rejects or modifies analysis results performed by the central processing device 170, the central processing device 170 can record the confirmation, acceptance, rejection or modification. When the central processing device 170 analyzes similar data again, it can analyze that data according to the health care professional's confirmation, acceptance, rejection or modification. If the original analysis was performed by a monitoring apparatus in the ambulatory subsystem, the central processing device 170 can transmit new configuration settings to the monitoring apparatus that originally performed the analysis. The configuration settings of the monitoring apparatus are altered according to the health care professional's confirmation, acceptance, rejection or modification. For example, when a health care professional rejects a tachycardia reported by a monitoring apparatus in the ambulatory subsystem 112, the central processing device 170 can learn from the rejection and send new configuration settings to the monitoring apparatus to change the detection threshold settings of the monitoring apparatus to avoid identifying a tachycardia when the similar heart rate data is detected again.

The real-time analysis ambulatory subsystem 112 can provide real-time monitoring for one or more patients at the same time and can report the data associated with the monitoring to the central processing subsystem 113. The central processing device 170 can be configured to store and analyze the results received from the multiple monitoring apparatuses. The central processing device 170 can report its analysis of the data received from the ambulatory subsystem 112 for multiple patients to various health care professionals assigned to monitor each respective patient. The central processing device 170 can also perform comparative studies among certain patient populations and certain medical conditions. The central processing device 170 can also perform comparative studies of monitoring and diagnostic results for a single patient across two different periods of monitoring. The central processing subsystem can perform a clinical review on the analysis results generated by the ambulatory subsystem, by the central processing device 170, or both. The clinical review can be initiated by a clinical care professional 190, 195, 198 or be performed automatically by the central processing device 170.

The monitoring and diagnostic responsibilities for each patient being monitored in the ambulatory subsystem 112 can be distributed between the monitoring apparatus for each patient and the central processing subsystem 113. In some examples, a monitoring apparatus, e.g. 107, can be configured to send all raw data to the central processing device 170 for analysis, while another monitoring apparatus, e.g. 108, can be configured to perform analysis of a physiological signal at the monitoring apparatus and send the analysis results to the central processing subsystem 113 where the central processing device 170 can confirm the results. In like manner, a third monitoring apparatus, e.g. 109, can be configured to perform an initial analysis of raw data associated with a physiological signal (e.g. identification of heart beats) and send only a portion of the analysis results or raw data to the central processing device for further analysis (e.g. identification of heart rate variability).

In some examples, the monitoring and diagnosis functions can be redistributed between a monitoring apparatus and the central processing subsystem 113. Multiple monitoring apparatuses in the ambulatory subsystem can each have a different distribution of monitoring and analysis responsibilities and the distribution for each monitoring apparatus can be changed while the patient is still attached to an ambulatory monitor. For example, a health care professional can request that a type or amount of analysis performed by a monitoring apparatus be changed. In one such example, a health care professional may determine that the real-time analysis of raw physiological signal data should be changed from a particular monitoring apparatus to the central processing device 170. The central processing device 170 sends new configuration settings to the monitoring apparatus to make the changes requested by the health care professional.

Figure 2:
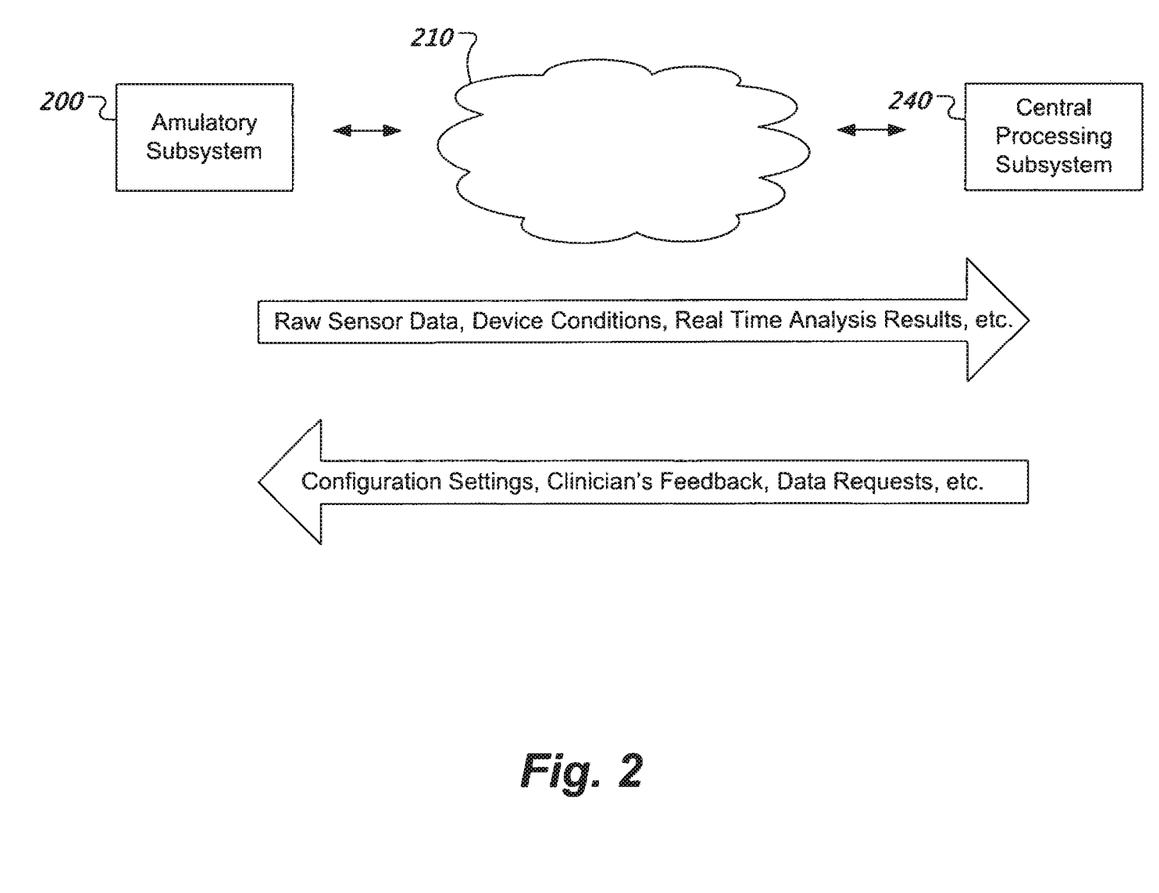
FIG. 2 shows an example of data that can be transmitted between an ambulatory subsystem and a central processing subsystem.

FIG. 2 shows an example of the data that can be transmitted between an ambulatory subsystem 200 and a central processing subsystem 240. The ambulatory subsystem 200 and the central processing subsystem 240 can work interactively. And, the monitoring and diagnostic capabilities can be distributed between the ambulatory subsystem 200 and the central processing subsystem 240.

The ambulatory subsystem 200 can send raw physiological data, analysis results, alarms, patient symptoms and/or device status or conditions (e.g. temperature in the device, resource usage and availability, battery status, signal strength, etc.) to the central processing subsystem over the network 210. The central processing subsystem 240 can perform central processing on that data and directly receive a health care professionals feedback. The central processing subsystem 240 can transmit via network 210 a health care professional's feedback and/or configuration settings to the ambulatory subsystem 200 to adjust the monitoring and diagnostic settings of a monitoring apparatus in the ambulatory subsystem 200. The central processing subsystem 240 can also send a request to the ambulatory subsystem 200 to get specific data.

Figure 3:
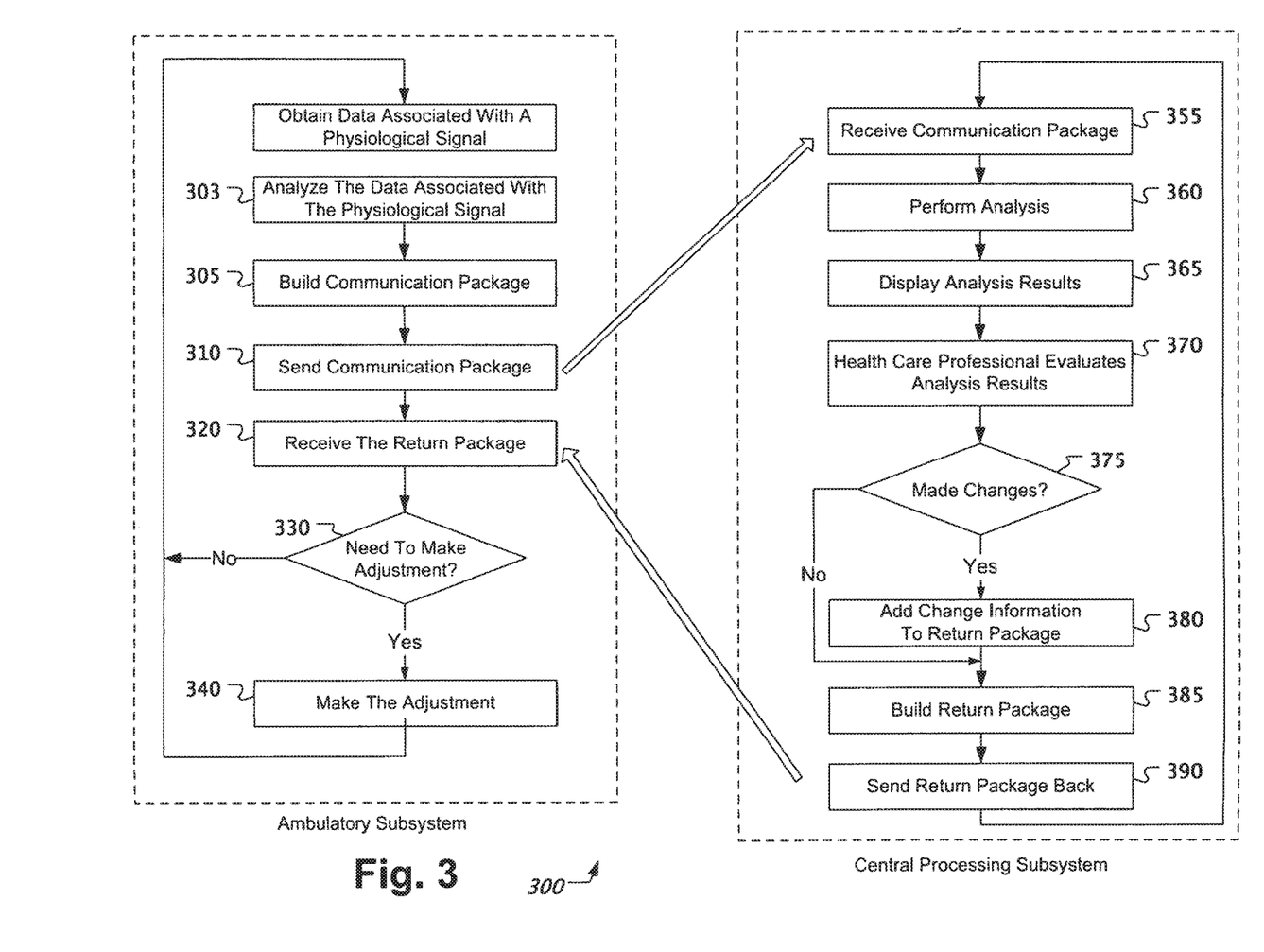
FIG. 3 shows an example process for interactive communication between an ambulatory subsystem and a central processing subsystem.

FIG. 3 shows an example process 300 for interactive communication between an ambulatory subsystem and a central processing subsystem. At 302, a monitoring apparatus obtains data associated with a physiological signal, such as sensor data. At 303, the monitoring apparatus analyzes the data associated with the physiological signal. At 305, the monitoring apparatus builds a communication package. The communication package can include data associated with the real-time analysis, such as analysis results, raw sensor data, information about the monitor, etc. The communication package can also include other data such as patient feedback data (e.g. patient input symptoms), patient identifier data, etc. At 310, the ambulatory subsystem sends the communication package to the central processing subsystem. In some examples, if there is a time delay before the ambulatory subsystem receives a return package at 320 from the central processing subsystem, the monitoring apparatus that sent the information can continue to obtain and analyze real-time data, such as a sensor data, and to build communication packages to be sent to the central processing subsystem.

At 355, the central processing subsystem waits to receive the communication package. Once a communication package is received from the ambulatory subsystem, the central processing subsystem performs analysis of the data received at 360. At 365, the central processing subsystem displays the results of the analysis performed at 360. The central processing subsystem can also display the data received from the real-time subsystem. The display can include a computer screen, a facsimile, or a print-out or the like. At 370, a health care professional such as a clinician evaluates the analysis results and the received data provided by the central processing system 113 The health care professional can provide feedback such as accept, modify, or reject real-time or central processing results. Feedback can also include changes to configuration settings. In some examples, the central processing system 113 can provide changes based on the analysis performed at 360. At 375, the process determines whether any changes were made, for example, by the health care professional. If so, the process 300 adds information regarding the changes to the return package 380 and builds a return package 385. The return package can include, for example, changes to the configuration settings (e.g. changes to the real-time analysis algorithms, the type of data transmitted to the central processing subsystem, etc.). If not, the process proceeds to building a return package 385; in the return package, the process indicates that no changes were made. At 390, the system sends the return package back to the monitoring apparatus that originally sent the data at 310 in the ambulatory subsystem.

When the monitoring apparatus in the ambulatory subsystem receives the return package at 320, the monitoring apparatus determines whether adjustments need to be made based on the return package. If not, then the process 300 returns to the beginning of the process 300. If so, then the monitoring apparatus makes the adjustments accordingly at 340 and proceeds to the beginning of the process 300. The process 300 can be repeated with the adjustments made at 340.

Figure 4:
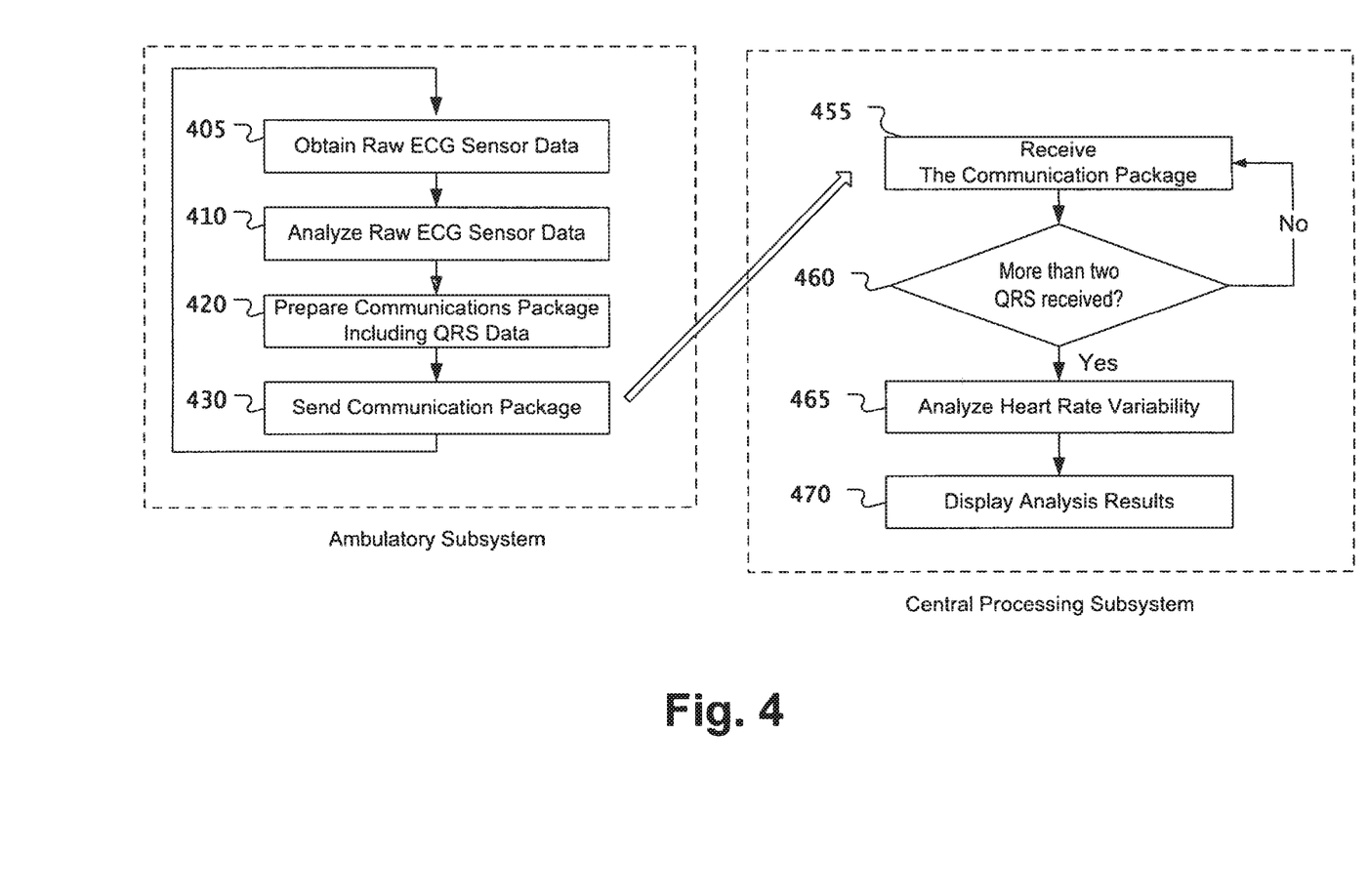
FIG. 4 shows an example process for interactive analysis of ECG data.

FIG. 4 shows an example process for interactive analysis of ECG data. At 405, the monitoring apparatus obtains raw ECG data from a sensor or sensors. At 410, the monitoring apparatus analyzes the raw ECG sensor data to detect a QRS complex. QRS data can be used to determine arrhythmia events, such as ventricular tachycardia. QRS data can also be used in further analysis, such as in performing a heart rate variability analysis. The QRS complex represents ventricular contraction of a heart. The monitoring apparatus can identify various fiducial points in the QRS complex such as onset of the ventricular contraction, the peak of the ventricular contraction, and the termination of the ventricular contraction. Heart rate variability refers to the beat-to-beat alterations in heart rate and can be calculated once multiple subsequent QRS complexes are identified. ECG data from a single heart beat can be represented by multiple data points. For example, at a heart rate of 60 Beats Per Minutes (BPM), there is one QRS in every second. At an example sample rate of 250 ECG samples per second, the monitoring apparatus processes 250 samples for one heart beat. At 420, the monitoring apparatus prepares a communication package including the QRS data. The communication package can include other data as well. In some examples, the monitoring apparatus can be configured to include in the communications package only certain portions of the data associated with the analysis results of the QRS complex. For example, the communications package can include the detected fiducial points for each heart beat instead of all 250 raw ECG data points. At 430, the monitoring apparatus can transmit the communication package including the fiducial points to the central processing subsystem. The monitoring apparatus can then return step 405 and begin the process again.

At 455, the central processing subsystem receives the communications package from the ambulatory subsystem. At 460, the central processing subsystem determines whether more than two communications packages including QRS data have been received. If not, the central processing subsystem returns to step 455 to receive another communication package from the ambulatory subsystem. If more than two communications packages including QRS data have been received, the central processing subsystem determines the heart rate variability at 465. Various algorithms can be used to analyze heart rate variability, such as comparing the RR intervals, etc. At 470, the analysis results can be displayed. In some examples, a return package that includes changes based on the analysis performed by the ambulatory subsystem, can be sent back to the ambulatory subsystem, as described in connection with FIG. 3. Also, in some examples, the process can be repeated such that the ambulatory subsystem provides updated QRS data to the central processing subsystem, and the central processing subsystem calculates and updates the heart rate variability data as the QRS data is received.

Some or all of the QRS data and the raw ECG data can be stored in the monitoring apparatus. If the central processing subsystem determines it needs more information regarding a particular QRS complex, a request for more data can be sent to the monitoring apparatus. In some examples, the monitoring apparatus can temporarily store the analysis data and raw sensor data, till a return package is received confirming that no additional data has been requested by the central processing subsystem. If a confirmation is received, the stored data can be deleted to free-up storage space in the monitoring apparatus. In another example, circular data buffer can be used to always save the new data.

Performing QRS detection in the real-time subsystem can avoid transmitting large quantity of raw ECG data to the central processing subsystem. This can preserve bandwidth for transmitting other information, such as the heart rate, annotations, detected arrhythmias. Having cardiac arrhythmia analysis performed at the central processing subsystem provides flexibility for health care professionals to request various analyses for various patients. For example, cardiac arrhythmia analysis can include many different statistical measurements, frequency domain measurements, and graphics presentations. Moreover, different doctors may require different sets of measurements.

If a new analysis algorithm, such as a new measurement, is introduced, the new analysis algorithm can be installed in the central processing subsystem, such as in the central processing device 170, and can be used to analyze data received from multiple monitoring apparatuses in the ambulatory subsystem. This provides a mechanism for updating a single central processing device rather than updating multiple remote ambulatory monitoring apparatuses in the field.

In other implementations, the central processing subsystem can perform high level analysis of the results generated by the ambulatory subsystem and received by the service/data center. For example, the central processing subsystem can receive QRS data from the ambulatory subsystem and can use R-R intervals to perform a heart rate variability analysis. Based on the results of this analysis, the central processing subsystem can provide diagnosis for respiratory conditions, such as sleep apnea or sleep disorders.

The disclosed systems, techniques, and all of the functional operations described and illustrated in this specification can be implemented in digital electronic circuitry, or in computer hardware, firmware, software, or in combinations of the forgoing. For example, one or more computers and/or circuitry can be operable to or configured and arranged to perform the functions and techniques disclosed herein. Apparatuses and/or systems can be implemented using a software product (e.g., a computer program product) tangibly embodied in a machine-readable storage device for execution by a programmable processor, and processing operations can be performed by a programmable processor executing a program of instructions to perform functions by operating on input data and generating output. Further, the system can be implemented advantageously in one or more software programs that are executable on a programmable system. This programmable system can include the following: 1) at least one programmable processor coupled to receive data and instructions from, and to transmit data and instructions to, a data storage system; 2) at least one input device; and 3) at least one output device. Moreover, each software program can be implemented in a high-level structured or object-oriented programming language, or in assembly or machine language if desired; and in any case, the language can be a compiled or an interpreted language.

Also, suitable processors include, by way of example, both general and special purpose microprocessors. Generally, a processor will receive instructions and data from a read-only memory, a random access memory, and/or a machine-readable signal (e.g., a digital signal received through a network connection). The essential elements of a computer are a processor for performing instructions and one or more memory devices for storing instructions and data. Generally, a computer will include one or more mass storage devices for storing data files. Such devices can include magnetic disks, such as internal hard disks and removable disks, magneto-optical disks, optical disks, and flash memories. Storage devices suitable for tangibly embodying software program instructions and data include all forms of non-volatile memory, including, by way of example, the following: 1) semiconductor memory devices, such as EPROM (electrically programmable read-only memory); EEPROM (electrically erasable programmable read-only memory) and flash memory devices; 2) magnetic disks such as internal hard disks and removable disks; 3) magneto-optical disks; and 4) CD-ROM disks. Any of the foregoing can be supplemented by, or incorporated in, ASICs (application-specific integrated circuits).

The disclosed systems and techniques, described and illustrated in this specification can be implemented using one or more communications networks such as a wired or wireless network. Examples of communication networks include, e.g., a local area network ("LAN"), a wide area network ("WAN"), the Internet or any combinations of such. The communications network can also include a landline telephone network, a wireless network, a cellular network, a satellite communication network, or other suitable network to facilitate two-way communication. The communication network may also include WIFI or WiMAX.

To provide for interaction with a user (such as the health care professional), the system can be implemented on a computer system having a display device such as a monitor or LCD (liquid crystal display) screen for displaying information to the user and a keyboard and a pointing device such as a mouse or a trackball by which the user can provide input to the computer system. The computer system can be programmed to provide a graphical user interface through which computer programs interact with users.

A number of embodiments of the invention have been described. Nevertheless, it will be understood that various modifications may be made without departing from the spirit and scope of the invention. For example, the disclosed operations can be performed in a different order and still achieve desirable results. Accordingly, other embodiments are within the scope of the following claims.

What is claimed is:

1. A system for monitoring a patient, the system comprising:
   an implantable ambulatory monitoring apparatus configured to be implanted in a living being and configured to obtain physiological signal data from the living being, perform a first analysis of the data, and wirelessly transmit a subset of the data associated with the first analysis, the subset of the data being less than all of the data associated with the first analysis, wherein the subset is identified based on the first analysis of the data by the ambulatory monitoring apparatus;
   a central processing device, remote from the implantable ambulatory monitoring apparatus and configured to wirelessly receive from the monitoring apparatus the subset of the data associated with the first analysis, perform a second analysis of the data, and wirelessly transmit analysis results associated with the second analysis to the ambulatory monitoring apparatus, wherein the second analysis identifies a health-related anomaly; and
   a display configured to receive the analysis results associated with the second analysis from the central processing device and visually display the analysis results;
   wherein the ambulatory monitoring apparatus is further configured to wirelessly transmit, in response to receiving the analysis results associated with the second analysis from the central processing device, a portion of the received data associated with the second analysis to the central processing device to validate the identified health-related anomaly;
   wherein the ambulatory monitoring apparatus receives, from the central processing device, a return package comprising one or more adjustments or one or more settings of the ambulatory monitoring apparatus, wherein the one or more adjustments are based on the analysis results displayed via the display; and
   wherein the ambulatory monitoring apparatus implements the one or more adjustments of the one or more settings.

2. The system of claim 1, wherein a wireless transceiver is coupled to the monitoring apparatus.

3. The system of claim 2, wherein the wireless transceiver is further configured to send the physiological signal identifying the health-related anomaly over a cellular network.

4. The system of claim 1, wherein the health related anomaly is an arrhythmia event.

5. The system of claim 1, further comprising a memory configured to store the physiological signal data.

6. The system of claim 5, wherein the memory is configured to store the physiological signal data in a circular buffer.

7. The system of claim 1, further comprising at least one sensor configured to be coupled to the living being, wherein the monitoring apparatus is configured to receive the physiological data from the at least one sensor.

8. The system of claim 1, wherein the physiological data comprises ECG data.

9. The system of claim 8, wherein the subsets of the physiological data associated with the first analysis and second analysis comprise fiducial points of a QRS complex.

10. A method for monitoring a patient, the method comprising:
    obtaining, via an implantable monitoring apparatus implanted in a living being and, physiological signal data for a living being, and performing a first analysis of the data;
    wirelessly transmitting, from the implantable monitoring apparatus, a subset of the data associated with the first analysis, to a central processing device, and performing a second analysis of the data at the central processing device, the subset of the data being less than all of the data associated with the first analysis, wherein the second analysis identifies a health-related anomaly;
    generating, based on the second analysis of the data at the central processing device, analysis results;
    transmitting, from the central processing device, the analysis results associated with the second analysis to the ambulatory monitoring apparatus;
    transmitting, from the ambulatory monitoring apparatus in response to receiving the analysis results associated with the second analysis from the central processing device, a portion of the received data associated with the second analysis to the central processing device to validate the identified health-related anomaly;
    transmitting, from the central processing device, the analysis results associated with the second analysis to a display;
    visually displaying the analysis results via the display, receiving, by the ambulatory monitoring apparatus from central processing device, a return package comprising one or more adjustments or one or more settings of the ambulatory monitoring apparatus, wherein the one or more adjustments are based on the analysis results displayed via the display; and
    implementing, at the ambulatory monitoring apparatus, the one or more adjustments of the one or more settings.

11. The method of claim 10, wherein a wireless transceiver is coupled to the monitoring apparatus.

12. The method of claim 11, wherein the wireless transceiver is further configured to send the physiological signal identifying the health-related anomaly over a cellular network.

13. The method of claim 10, wherein the health related anomaly is an arrhythmia event.

14. The method of claim 10, further comprising a memory configured to store the physiological signal data.

15. The method of claim 14, wherein the memory is configured to store the physiological signal data in a circular buffer.

16. The method of claim 10, further comprising at least one sensor coupled to the living being, wherein the monitoring apparatus is configured to receive the physiological data from the at least one sensor.

17. The method of claim 10, wherein the physiological data comprises ECG data.

18. The method of claim 17, wherein the subsets of the physiological data associated with the first analysis and second analysis comprise fiducial points of a QRS complex.

\* \* \* \* \*